(12) United States Patent  
Moore, Jr.

(10) Patent No.: US 8,439,938 B2
(45) Date of Patent: May 14, 2013

(54) VARIABLE FREQUENCY PHACOEMULSIFICATION HANDPIECE

(75) Inventor: Thomas G. Moore, Jr., Kirkwood, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 731 days.

(21) Appl. No.: 12/341,427

(22) Filed: Dec. 22, 2008

(65) Prior Publication Data

US 2010/0160852 A1    Jun. 24, 2010

(51) Int. Cl.
*A61F 9/00* (2006.01)
(52) U.S. Cl.
USPC .................................................. 606/166
(58) Field of Classification Search ............ 606/107, 606/166, 169, 170, 171
See application file for complete search history.

(56) References Cited

U.S. PATENT DOCUMENTS

| | | |
|---|---|---|
| 6,283,974 B1 | 9/2001 | Alexander |
| 6,716,219 B1 * | 4/2004 | Koch ............................ 606/107 |
| 2004/0092921 A1 | 5/2004 | Kadziauskas |

OTHER PUBLICATIONS

Article: Sonochemistry Author: Kenneth S. Suslick Science, vol. 247 Mar. 23, 1990 pp. 1439-1445.
Article: The Physics of Phaco: A Review Authors: Mark Packer, MD, William J. Fishkind, MD, I. Howard Fine, MD, Barry S. Seibel, MD, and Richard S. Hoffman, MD J Cataract Refractive Surg; vol. 31, Feb. 2005—2005 ASCRS and ESCRS Update/Review pp. 424-431.
International Search Report (PCT/ISA/210) and Written Opinion (PCT/ISA/237) mailed on Apr. 9, 2010.

* cited by examiner

*Primary Examiner* — Ryan Severson
*Assistant Examiner* — Jonathan W Miles
(74) *Attorney, Agent, or Firm* — Jeffrey B. Powers

(57) ABSTRACT

A phacoemulsification system includes a phacoemulsification handpiece having a horn coupled to a transducer configured to convert alternating current into mechanical oscillation of the horn. The phacoemulsification handpiece further includes a phacoemulsification needle attached to the horn. The phacoemulsification needle vibrates by oscillation of the horn, to provide for mechanical cutting of tissue and inducing cavitation proximate a tip of the phacoemulsification needle. The phacoemulsification system further includes a control system with associated drive circuitry in connection with the transducer of the phacoemulsification handpiece. The control system is configured to adjust an operating frequency of the transducer to increase or decrease a mechanical cutting performance and a cavitational-induced performance of the phacoemulsification needle.

9 Claims, 4 Drawing Sheets

US 8,439,938 B2

VARIABLE FREQUENCY PHACOEMULSIFICATION HANDPIECE

FIELD

The present invention relates to ophthalmic microsurgical instruments, and more particularly to a phacoemulsification handpiece for use in ophthalmic surgery.

BACKGROUND

This section provides background information related to the present disclosure which is not necessarily prior art.

Ophthalmic surgery often involves cutting away or emulsifying tissues that need to be removed from the eye, such as in cataract surgery. Surgery is performed using a phacoemulsification handpiece having a needle with a cutter at its distal end and is inserted into the eye through an incision. The cutting tip of the needle oscillates to establish a cutting action for fragmentation of tissue. The oscillating nature of the needle also induces cavitation near the tip of the needle. For efficiency reasons, commercially available phaco-emulsification handpieces are designed to operate at a single fixed resonant frequency, which is based on the geometry of the phacoemulsification handpiece. Thus, each handpiece design has a single oscillation frequency and a fixed degree of cavitation-induced emulsification associated with the fixed resonant frequency.

SUMMARY

This section provides a general summary of the disclosure, and is not a comprehensive disclosure of its full scope or all of its features. The present disclosure relates to systems for oscillating a phaco-emulsification needle for use in ophthalmic surgery. According to one aspect of the present disclosure, a phaco-emulsification system is provided that comprises a phaco-emulsification handpiece and a control system. The phacoemulsification handpiece has a horn coupled to a transducer that is configured to convert alternating current into mechanical oscillation of the horn. The phacoemulsification handpiece further includes a phacoemulsification needle that is attached to the horn. The phacoemulsification needle includes a passage through which fluid and/or emulsified tissue may be aspirated. A sleeve is sometimes coaxially disposed about the phacoemulsification needle so as to define an annular passage between the phacoemulsification needle and the sleeve, for introducing irrigation fluid into a surgical site. The phacoemulsification needle is vibrated by oscillation of the horn. The needle vibration provides for cutting of tissue and/or inducing cavitation proximate the tip of the phacoemulsification needle. The phacoemulsification system further comprises a control system having a console that includes an associated drive circuitry in connection with the transducer of the phacoemulsification handpiece. The control system is configured to selectively adjust the operating (oscillating) frequency of the transducer and vary the operating frequency of the phacoemulsification needle, to thereby increase or decrease the mechanical cutting performance and/or the cavitational-induced performance.

According to another aspect of the present disclosure, a method is provided for operating the control system to control a phacoemulsification handpiece. The method comprises operating the drive circuitry of a control system that is in connection with the transducer, to oscillate the transducer at a select operating frequency. The method further comprises monitoring the oscillation of the transducer, to determine if the transducer has been continuously oscillating at the same operating frequency for more than a maximum time duration. Upon determining that the transducer has been continuously oscillating at the same operating frequency for more than a maximum duration of time, the method controls the drive circuitry of the control system to automatically change the operating frequency of the transducer.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. The following description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Figure 1:
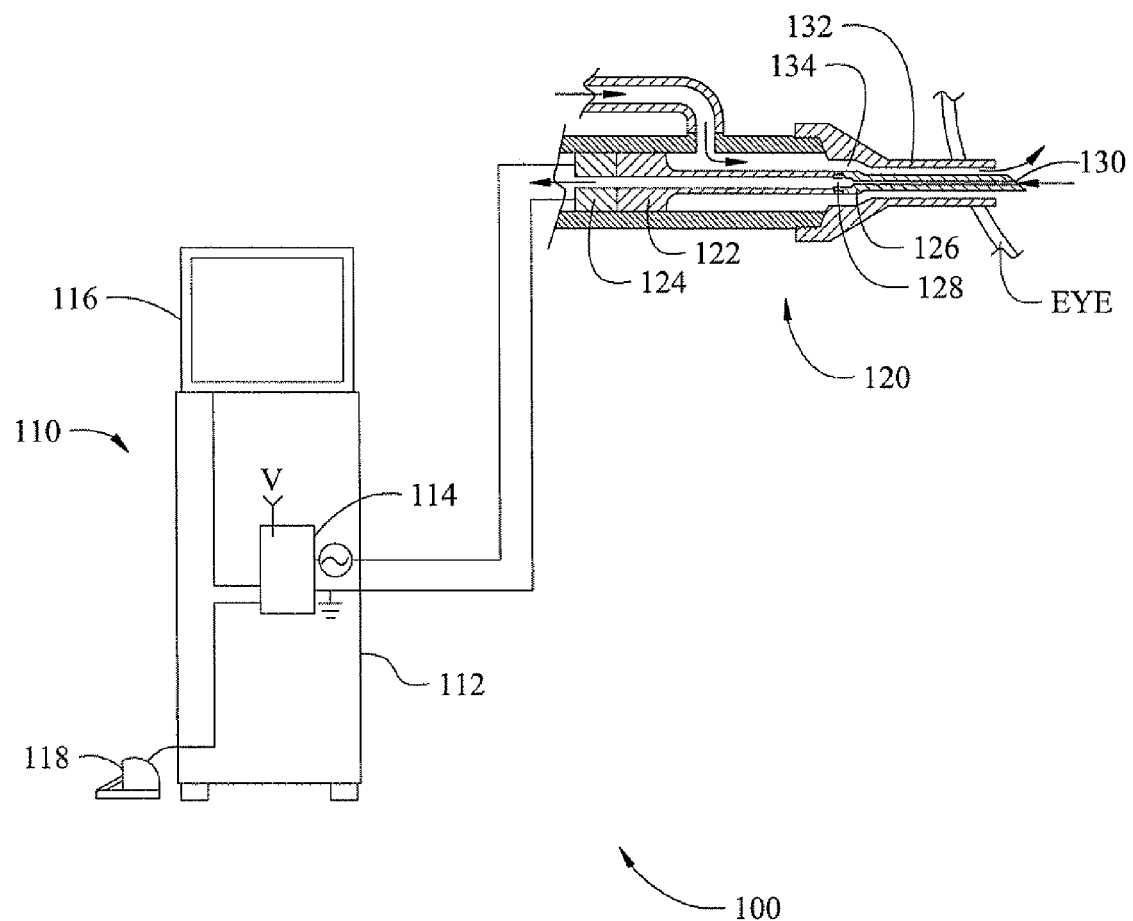
FIG. 1 shows one embodiment of a phacoemulsification system with a cross-sectional view of a phacoemulsification handpiece, in accordance with the principles of the present disclosure.

Referring to FIG. 1, a phacoemulsification system 100 includes a control system 110 for controlling a phacoemulsification handpiece 120. The phacoemulsification system 100 generally includes a phacoemulsification handpiece 120 having a horn 122 coupled to a transducer 124 that is configured to convert high-frequency alternating current into mechanical oscillation of the horn 122. Only one transducer 124 is shown but typically a plurality of transducers 124 are stacked together. The phacoemulsification handpiece 120 further includes phacoemulsification needle 126 that is attached to the horn 122. The phacoemulsification needle 126 has a passage 128 therein, through which fluid and/or emulsified tissue may be aspirated. The phacoemulsification handpiece further may include a sleeve 132 coaxially disposed about the phacoemulsification needle 126 so as to define an annular passage 134 between the phacoemulsification needle 126 and the sleeve 132. The sleeve 132 accordingly provides an irrigation fluid passage 134 for introducing irrigation fluid into a surgical site. The phacoemulsification needle 126 is made to vibrate by the oscillation of the horn 122, to provide for cutting of tissue and/or inducing cavitation proximate the tip of the phacoemulsification needle. The oscillation of horn 122 is caused by transducer 124. The vibration of the phacoemulsification needle 126 causes fragmentation and emulsification of tissue at the surgical site.

The phacoemulsification system further includes a control system 110 comprising a console 112 having an associated drive circuitry 114 in connection with the transducer 124 of the phacoemulsification handpiece 120. The associated drive circuitry 114 is in connection with a power source (not shown), and is configured to provide a variable frequency alternating current to drive or excite the transducer 124 at a select operating frequency. The control system 110 is configured to control the associated drive circuitry 114 to selectively adjust the operating frequency of the transducer 124, based, in part, on inputs to the control system 110. Thus, the control system 110 is configured to vary the vibration of the phacoemulsification needle 126, to increase or decrease the mechanical cutting performance and/or cavitational-induced performance of the phacoemulsification needle 126. The control system 110 further receives inputs from an operator, to permit selection of a specific operating frequency, for example. The input may be provided by an input device 116, which may comprise a keyboard or display device associated with the console 112, or buttons (not shown) on the console 112, for example. The control system 110 may further include a foot pedal 118, which an operator may depress or release to provide input to the control circuit 110 for adjusting the operating frequency of the transducer 124.

Figure 2:
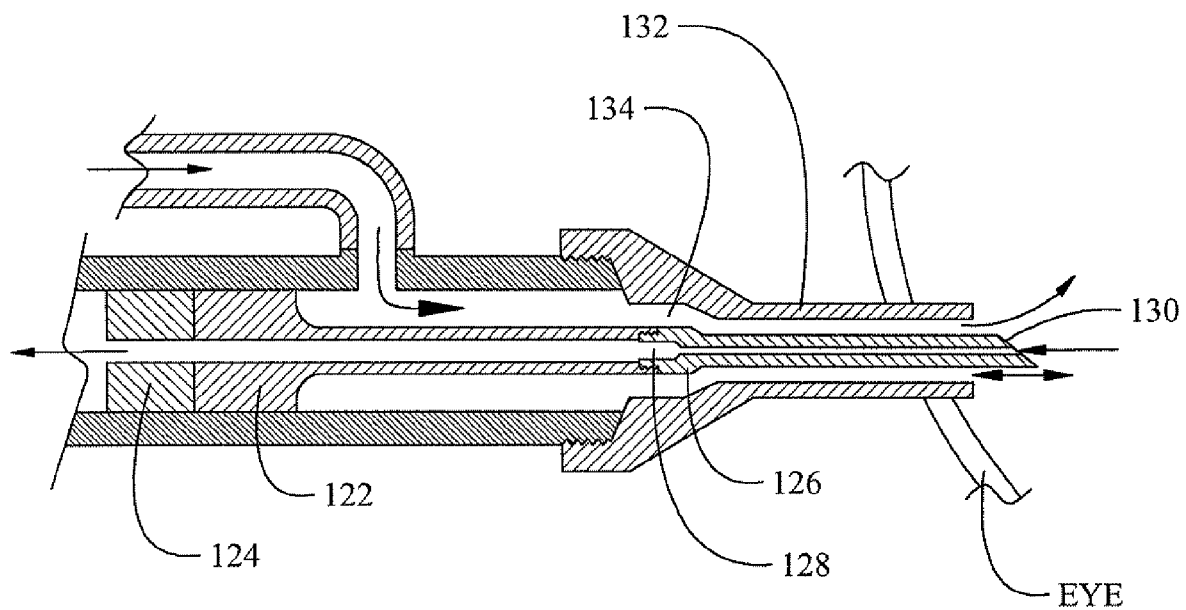
FIG. 2 shows a cross-sectional view of the phacoemulsification handpiece shown in FIG. 1, in accordance with the principles of the present disclosure.

Referring to FIG. 2, the phacoemulsification handpiece device includes a horn 122 that is mechanically coupled to one or more transducers 124, which convert high-frequency alternating current into mechanical vibrations in the range of 15 to 60 kilohertz (kHz). The transducer 124 for producing the vibrations or oscillations may be a magnetostrictive transducer or a piezoelectric transducer. In the case of a magnetostrictive transducer, a magnetic field that is induced by a high-frequency electric current flowing through a coil of the magnetostrictive transducer excites the oscillation. In a piezoelectric transducer, an electric current applied to a crystal of the piezoelectric transducer causes the crystal to contract. A high frequency alternating current applied to the crystal will cause the piezoelectric crystal to oscillate at the frequency of the applied current. When oscillations are produced at the resonant frequency of an oscillation path comprised of the material of the transducer 124 combined with the horn and needle, the transformation into mechanical amplitude will be optimal and the creation of heat will be minimized.

The phacoemulsification handpiece device 120 further includes a phacoemulsification needle 126 attached to the horn 124, and has a passage 128 formed in the needle 126 and horn 124 through which fluid and/or emulsified tissue may be aspirated. The phacoemulsification needle 126 may be made of titanium or titanium alloy, such as a 19 or 20 gauge titanium, for example. Of course the needle 126 may also be formed of other metals, ceramics, or plastics that may be suitable for ophthalmic surgery. The phacoemulsification needle 126 is suited for use in ophthalmic surgical procedures, such as extracapsular cataract extraction via phacoemulsification, for example. In order to remove a cataract through a small incision, it is necessary to break up the hard cataract into emulsate for aspiration. The phacoemulsification needle 126 has a tip 130 that may be rapidly moved back and forth to provide a mechanical cutting action, or jackhammer effect, for breaking up tissue. The back and forth movement of the phacoemulsification needle 126 is defined as the stroke length or longitudinal excursion, which may be in the range of 5 to 100 microns. The mechanical disruption caused by the stroke length is associated with the operating frequency at which the phacoemulsification needle 126 is vibrated. The phacoemulsification needle 126 is vibrated by the mechanical oscillation of the horn 122 coupled to the transducer 124. While the present example is directed to linear oscillation, the present invention may also be applied to torsional or transverse oscillation of the needle as is known.

The phacoemulsification handpiece device 120 further may include a sleeve 132 coaxially disposed about the phacoemulsification needle 126 so as to define an annular passage 134 between the phacoemulsification needle 126 and the sleeve 132, for introducing irrigation fluid into a surgical site. The irrigation fluid delivered to the surgical site may be a balanced salt solution, for example. Accordingly, irrigation fluid may be fed via the sleeve 132 to a surgical site proximate the phacoemulsification needle tip 130, and fluid or emulsate may be aspirated through the passage 128 in the center of the phacoemulsification needle 126.

The vibration or oscillation of the phacoemulsification needle 126 causes direct mechanical cutting or fragmentation of tissue upon contact with the tissue, and also causes the radiation of ultrasonic energy into the surrounding tissue and fluid that results in cavitational effects. Cavitation is defined as the growth, oscillation, and implosive collapse of micron-sized bubbles in liquids under the influence of an acoustic field, and may be created when the phacoemulsification needle moves through a medium at ultrasonic speeds. When a cavitation bubble that forms can no longer sustain itself, the bubble or cavity implodes. The rapid cavitational collapse can produce shock waves and high speed jets of liquid, and can accelerate particles to high velocities. These effects can provide a mechanism for generating an impact against the surface of solids, where impingement of microjets and shock waves can create localized erosion of the surface. Thus, when the tip 130 of the phacoemulsification needle 126 is brought into contact or close proximity of the cataract, the cataract material is disrupted in a jackhammer fashion by the mechanical cutting energy from the phacoemulsification needle 126, and the cataract material is simultaneously emulsified by the implosion of cavitation bubbles generated from the rapid ultrasonic motion of the phacoemulsification needle 126.

All commercially available phacoemulsification handpieces operate at a single fixed resonant frequency or a single fixed resonant frequency for each direction of travel. For example a handpiece capable of both longitudinal and torsional vibration may have one resonant frequency for longitudinal vibration and a second resonant frequency for torsional vibration. Accordingly, each handpiece design has a level of mechanical disruption associated with its operating frequency, and a level of cavitation-induced emulsification that is also associated with its operating frequency. With regard to the mechanical disruption associated with the needle stroke length, the effect of the disruption is directly proportional to the operating frequency. For example, if a 20 kHz handpiece exhibits a mechanical disruption effect of 1.0, a 50 kHz handpiece will exhibit a mechanical disruption effect of 2.5, since its needle is traveling 2.5 times as fast at 50 kHz as a needle travelling at 20 kHz (see the graph of FIG. 3).

On the other hand, the relationship between frequency and cavitation-induced emulsification is not as clearly defined.

The diameter of cavitation bubbles generated in a homogeneous liquid is inversely proportional to the frequency of the oscillation generator (e.g., the crystal transducer of the phacoemulsification handpiece). Furthermore, the cavitational energy released by a bubble when it implodes (i.e., it rapidly collapses) is proportional to the bubble's volume. Since the volume of a sphere is proportional to the cube of the diameter of the sphere, the cavitation-induced emulsifying effect is inversely proportional to the operating frequency cubed. For example, if a 50 kHz phacoemulsification handpiece exhibits an emulsifying effect of 1.0, a 20 kHz phacoemulsification handpiece will exhibit an emulsifying effect of approximately 15.6 (i.e., $1/20^3/1/50^3 = 50^3/20^3 = 15.6$).

Following from the above, a handpiece operating at a given frequency (F) will have a specific or characteristic mechanical disruption level (M)/cavitation-induced emulsification level (C) performance ratio M/C, where the ratio is proportional to $F^4$ (i.e., $F/(1/F^3)$). For example, if a 20 kHz phacoemulsification handpiece has an M/C of 1.0, a 50 kHz phacoemulsification handpiece will have a relative M/C of 39.1 (i.e., $50^4/20^4$). Comparatively, a 35 kHz phacoemulsification handpiece will have an M/C of 9.37 (relative to the 20 kHz handpiece M/C of 1.0). In other words, high frequency handpieces have high mechanical performance and low cavitational performance, whereas low frequency handpieces have high cavitation performance and low mechanical performance.

Figure 3:
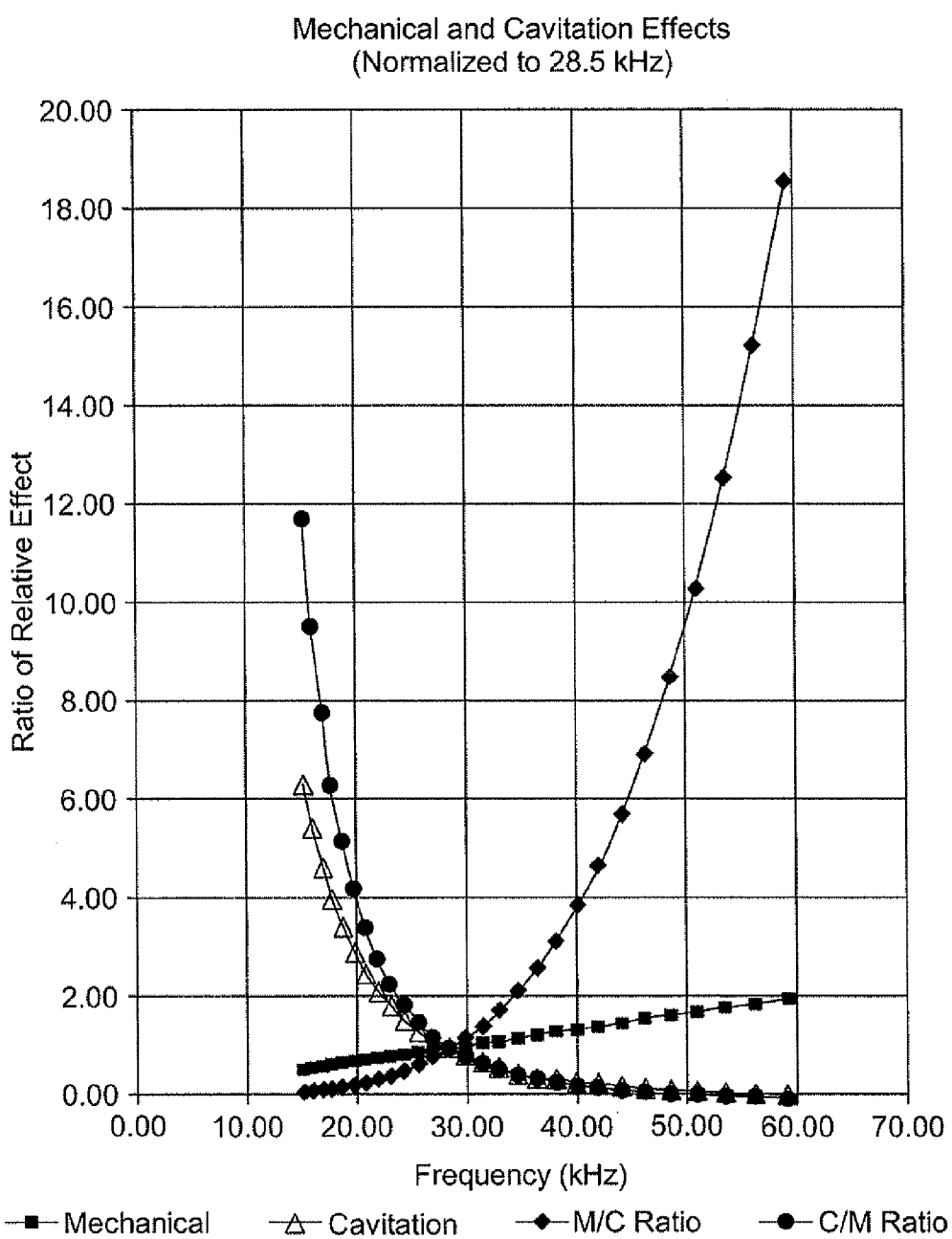
FIG. 3 shows a graph comparing the level of mechanical disruption and cavitation-induced emulsification, and ratios thereof, for a phacoemulsification needle in accordance with the principles of the present disclosure.

Referring to FIG. 3, a graph is shown that compares the level of mechanical disruption and cavitation-induced emulsification, and the performance ratios M/C and C/M. The data is normalized for a phacoemulsification handpiece with a frequency of 28.5 kHz. At 15 kHz, the C/M ratio is approximately 12.0 and at 60 kHz, the M/C ratio is approximately 19.0, yielding an overall dynamic adjustment range of 228.

According to one aspect of the present disclosure, the phacoemulsification system 100 includes a control system 110 that is configured to provide an adjustable ultrasonic operating frequency for the phacoemulsification handpiece 120. As shown in FIG. 1, the control system 110 comprises a console 112 having an associated drive circuitry 114 in connection with the transducer 124 of the phacoemulsification handpiece 120. The control system 110 further includes an input device 116 that enables an operator to provide an input for selection of a specific operating frequency, stroke length, or M/C ratio at which to operate the phacoemulsification needle 120. The control circuit 110 may further include a foot pedal 118, which an operator may depress or release to provide input to the control circuit 110 for adjusting the operating frequency of the transducer 124. The control system 110 is configured to receive an input of a desired operating frequency for the transducer, and to selectively adjust the operating frequency within a range of between about 15 kHz up to about 60 kHz. The control system 110 is further configured to adjust the operating frequency by at least a minimum of plus or minus 10% from the nominal operating frequency. As stated above, the level of mechanical disruption and cavitation-induced emulsification generated by the phacoemulsification needle 126 are both determined as a function of the operating frequency. The control system 110 allows an operator of the phacoemulsification system 100 to provide an input for adjusting or selecting an operating frequency so as to achieve a desired "mechanical disruption/cavitation-induced emulsification" performance ratio (i.e., the ratio of the mechanical disruption level relative to the cavitation-induced emulsification level). An effective range of operation for ophthalmic surgery is generally the above stated 15 kHz-60 kHz range. However, an effective system may operate over a much smaller range such as ±10%, ±20%, or ±30% off a nominal or resonant frequency (e.g. 28.5 kHz, 40 kHz, etc.) of a transducer stack. By varying the non-resonant operating frequency in a direct drive system around the nominal frequency of the transducer stack an effective excursion or longitudinal movement of the needle tip can still be achieved without very large driving amplitudes being applied to the stack. A ±10% range from a nominal frequency should still enable an effective trade off between mechanical disruption and cavitational emulsification to be achieved. Such a direct drive system is best realized using a transducer stack that will still achieve an effective excursion of each transducer without the need to be within a few hundred hertz of nominal. Such transducers are commercially available and include devices available from Physik Instrumente (PI) GmbH & Co. In this way a direct drive system would not rely on the amplification achieved in today's phaco systems by driving the transducer stack at resonance to obtain effective excursion of the needle tip. The physician may also provide an input of a desired ratio value, such as those shown in the graph in FIG. 3.

Other possible implementations should be apparent from the above disclosure. For example, it may be possible for a system according to the present invention to provide for mechanically changing the operating frequency by adding weight, length, or a change in geometry to the oscillation path.

Thus, the control system 110 is configured to selectively adjust the operating frequency of the transducer 124 to establish a desired ratio of the mechanical disruption level relative to the cavitation-induced emulsification level. The level of mechanical disruption level and the level of cavitation-induced emulsification are both determined as a function of the operating frequency. The level of mechanical disruption is proportional to the operating frequency, and the level of cavitation-induced emulsification is inversely proportional to the operating frequency. The control system 110 may also be configured to adjust the operating frequency to obtain a desired stroke length of the phacoemulsification needle tip 130, to thereby establish a desired combined mechanical and cavitation disruption level for providing the most effective cutting of the cataract.

In another aspect of the present disclosure, the control system may also be configured to automatically change the operating frequency after continuous oscillation at the same operating frequency for more than a maximum duration of time, in order to reduce heat generated by non-resonant frequency operation. During a procedure for removing a cataract, for example, when the phacoemulsification needle passes through aqueous tissue into a hard nucleus of a cataract, the resonant frequency will need to be adjusted to avoid inefficient emulsification, which may result in increased heat generation and prolonged duration of surgery. As previously stated, when oscillations are produced at the resonant frequency of the material of the transducer 124, horn 122, and phacoemulsification needle 126, the transformation into mechanical amplitude will be optimal and the creation of heat will be minimized.

Accordingly, when a physician establishes operation of the transducer 124 at a non-resonant frequency to achieve a desired cutting level or cavitation-induced performance, for example, sustained operation at the non-resonant frequency could result in increased heat generation that can cause damage to the eye. The present control system 110 may be configured to automatically adjust the operating frequency after the occurrence of continuous oscillation at the same operating frequency for more than a maximum duration of time. This ensures that the phacoemulsification handpiece will only operate at a given frequency for a limited period of time. The control system may also be configured to adjust or tune the operating frequency to the resonant frequency, to reduce heat generation. In addition, control system 110 may also pulse the oscillation of the transducer 124 in a variety of pulse schemes as is known, to reduce the amount of heat generated and to limit the amount of ultrasonic energy introduced into the eye.

The control system 110 may further be configured to iteratively change the operating frequency of the transducer 124 to prevent build up of heat generated by continuous operation at a non-resonant frequency for more than a transitory period of time. Where the transducer 124 has oscillated continuously at the same operating frequency for more than a given duration, the control system 110 may be configured to change the operation of the transducer 124 to a different operating frequency, which is randomly selected by the control system 110. A sequence of operating frequency changes may also be preprogrammed in control system 110.

Figure 4:
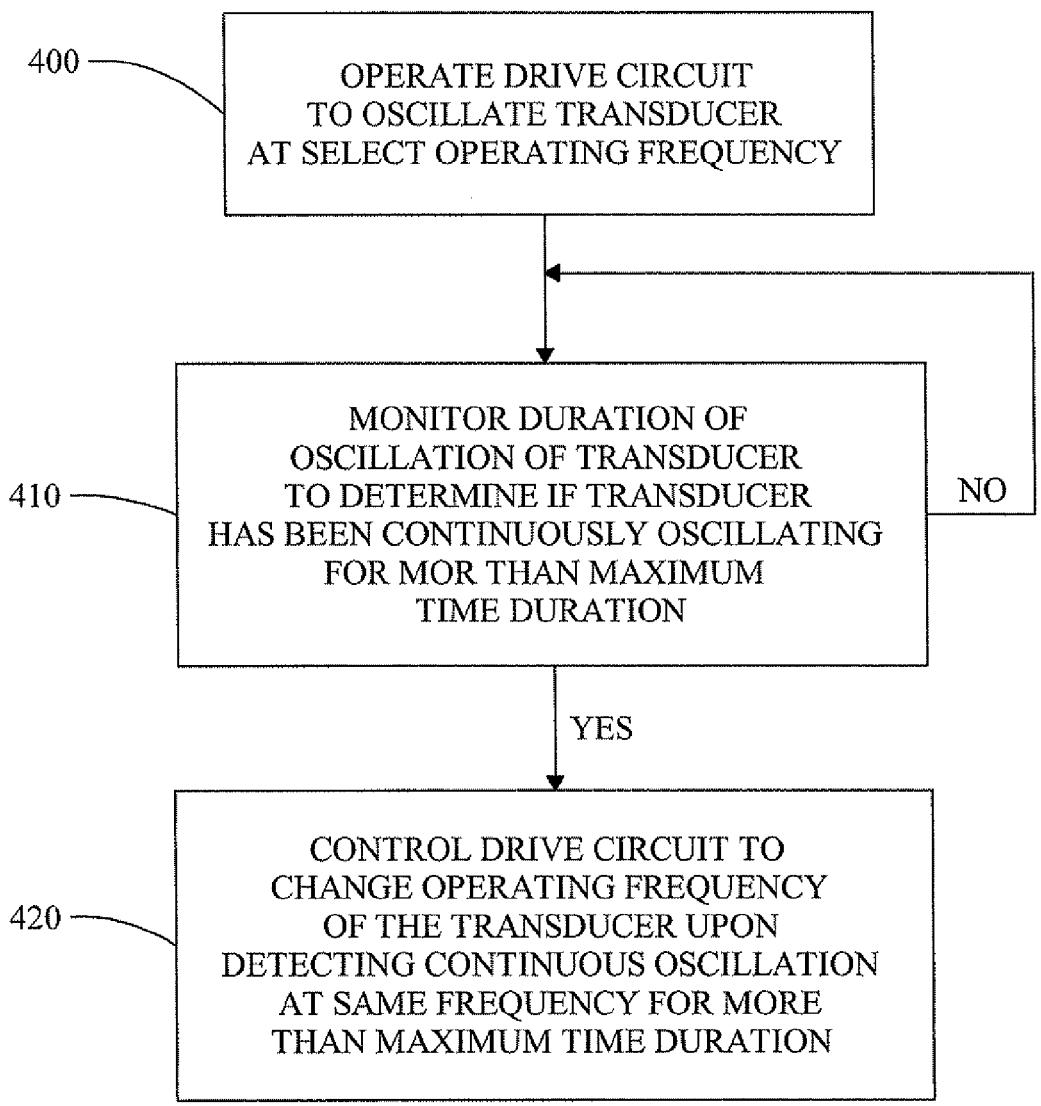
FIG. 4 shows a flow chart of a method for operating a control system for controlling a phacoemulsification handpiece, in accordance with the principles of the present disclosure.

In another aspect of the present disclosure, a method is provided for operating the control system 110 to control a phacoemulsification handpiece, which includes a transducer configured to convert alternating current into mechanical oscillation of a transducer coupled to a horn coupled to a phaco needle. Referring to FIG. 4, the method comprises operating a drive circuit of a control system that is in connection with the transducer at step 400, to oscillate the transducer at a select operating frequency. The method further comprises monitoring the oscillation of the transducer at step 410, to determine if the transducer has been continuously oscillating at the same operating frequency for more than a maximum duration of time. Upon determining that the transducer has been continuously oscillating at the same operating frequency for more than a maximum duration of time, the method calls for controlling the drive circuit of the control system to automatically change the operating frequency of the transducer at step 420. In the above method, the control system may be configured to change the operating frequency of the transducer to an optimal resonant frequency.

From the above, it may be appreciated that the present invention provides an improvement to control of a phacoemulsification handpiece. The present invention is illustrated herein by example, and various modifications may be made by a person of ordinary skill in the art. It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A phacoemulsification system for use in ophthalmic surgery, the phacoemulsification system comprising:
    a phacoemulsification handpiece having a horn coupled to a transducer that is configured to convert alternating current into mechanical oscillation of the horn, a phacoemulsification needle with an aspiration passage that is attached to the horn, whereby the phacoemulsification needle is made to vibrate by oscillation of the horn, to provide for mechanical cutting of tissue and inducing cavitation proximate a tip of the phacoemulsification needle, to thereby cause fragmentation of tissue at the surgical site; and
    a control system includes associated drive circuitry in connection with the transducer of the phacoemulsification handpiece device, the control system being configured to selectively adjust a non-resonant operating frequency of the transducer and vary the operating frequency of the phacoemulsification needle, to thereby increase or decrease a mechanical cutting performance and a cavitational-induced performance of the phacoemulsification needle wherein the phacoemulsification needle generates a level of mechanical disruption and a level of cavitation-induced emulsification that are both a function of the operating frequency, and the control system is configured to selectively adjust the operating frequency of the transducer to establish a desired ratio of the mechanical disruption level relative to the cavitation-induced emulsification level.

2. The phacoemulsification system of claim 1, wherein the control system is configured to selectively adjust the operating frequency of the transducer within a range of between about 15 kHz up to about 60 kHz.

3. The phacoemulsification system of claim 1 wherein the control system is configured to change the operating frequency of the transducer after oscillation at the same operating frequency for more than a maximum duration of time.

4. The phacoemulsification system of claim 3 wherein the control system is configured to adjust the operating frequency of the transducer to an optimal resonant frequency.

5. The phacoemulsification system of claim 1, wherein the transducer is a magnetostrictive transducer configured to be excited by the alternating electrical current applied to the magnetostrictive transducer.

6. The phacoemulsification system of claim 1, wherein the transducer is a piezoelectric crystal configured to be excited by the alternating electrical current applied to the piezoelectric crystal.

7. The phacoemulsification system of claim 1 wherein the level of mechanical disruption is proportional to the operating frequency, and the level of cavitation-induced emulsification is inversely proportional to the operating frequency.

8. The phacoemulsification system of claim 1 wherein the control system is configured to change the operating frequency of the transducer to prevent build up of heat that is generated by operation at non-resonant frequencies.

9. The phacoemulsification system of claim 8 wherein the control system randomly changes the operating frequency of the transducer.

* * * * *